United States Patent
Kroll

(10) Patent No.: US 7,181,281 B1
(45) Date of Patent: Feb. 20, 2007

(54) ICD USING MEMS FOR OPTIMAL THERAPY

(75) Inventor: Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 442 days.

(21) Appl. No.: 10/682,774

(22) Filed: Oct. 8, 2003

(51) Int. Cl.
*A61N 1/08* (2006.01)

(52) U.S. Cl. ............... 607/14; 607/4; 607/17; 607/18; 607/19

(58) Field of Classification Search ............ 607/4, 607/17–19, 20, 24, 14
See application file for complete search history.

(56) References Cited

U.S. PATENT DOCUMENTS

| | | | | |
|---|---|---|---|---|
| 4,712,555 | A | 12/1987 | Thornander et al. | 128/419 |
| 4,940,052 | A | 7/1990 | Mann et al. | 128/419 |
| 4,944,298 | A | 7/1990 | Sholder | 128/419 |
| 5,342,404 | A * | 8/1994 | Alt et al. | 607/6 |
| 5,458,622 | A * | 10/1995 | Alt | 607/15 |
| 5,466,254 | A | 11/1995 | Helland | 607/123 |
| 5,957,957 | A * | 9/1999 | Sheldon | 607/17 |
| 6,314,323 | B1 | 11/2001 | Ekwall | 607/25 |
| 6,477,421 | B1 * | 11/2002 | Andersen et al. | 607/19 |
| 6,539,253 | B2 | 3/2003 | Thompson et al. | 607/2 |
| 6,985,773 | B2 * | 1/2006 | Von Arx et al. | 607/32 |
| 2002/0095187 | A1 | 7/2002 | Thompson et al. | 607/6 |
| 2002/0115920 | A1 | 8/2002 | Rich et al. | 600/345 |
| 2003/0088160 | A1 * | 5/2003 | Halleck et al. | 600/300 |
| 2003/0158584 | A1 | 8/2003 | Cates et al. | 607/2 |

FOREIGN PATENT DOCUMENTS

| | | |
|---|---|---|
| WO | WO 01/00523 A1 | 1/2001 |
| WO | WO 03/011389 A2 | 2/2003 |
| WO | WO 03/011389 A3 | 2/2003 |

OTHER PUBLICATIONS

Mills, Jr., Roger M. et al., "Cardiac Arrhythmia and Hip Fracture", Int J Cardio., 1984; 6:382-385.
Morasso, Pietro G. et al., "Computing the COM From the COP in Postural Sway Movements", Human Movement Science, 1999; 18:759-767.
Owings, Tammy M. et al., "Maximum Recoverable Angle of Lean Does Not Differ Between Older Men and Women", Am Society Of Biomechanics, 25th Annual Meeting, San Diego, CA; 2001.
Lee, J. H. et al, "Prediction of Fall Risk in the Elderly: Time-Dependent Measures of Postural Sway Dynamics", Poster Session (0806), Orthopeadic Research Society, 47th Annual Meeting, San Francisco, CA; 2001.

* cited by examiner

Primary Examiner—Robert Pezzuto
Assistant Examiner—Shevon Johnson

(57) ABSTRACT

An exemplary method includes detecting movement of an in vivo oscillator using one or more in vivo sensors, receiving information from at least one of the one or more sensors, and deciding whether to switch an implanted cardiac therapy device from a lower tier of anti-arrhythmia therapy to a higher tier of anti-arrhythmia therapy based at least in part on the information. An exemplary implantable device includes a micro-electromechanical system (MEMS) capable of measuring acceleration and logic capable of determining postural sway based at least in part on acceleration measured by the MEMS. Various other exemplary methods, devices and systems are also disclosed.

25 Claims, 10 Drawing Sheets

| Dynamic Acceleration | Static Acceleration |
|---|---|
| $a_z = (V_z(t) - V_z(0))/t$ | Tilt z-component |
| $a_x = (V_x(t) - V_x(0))/t$ | Tilt x-component |
| $a_y = (V_y(t) - V_y(0))/t$ | Tilt y-component |

508

US 7,181,281 B1

ICD USING MEMS FOR OPTIMAL THERAPY

TECHNICAL FIELD

Exemplary methods, devices and/or systems presented herein generally relate to determining patient position and/or movement using an implanted cardiac therapy device having appropriate position and/or movement sensors.

BACKGROUND

In conventional tiered anti-arrhythmia therapy, decisions must be made as to when to switch from one tier to another. The timing of such decisions can in some instances be of little consequence; whereas, in other instances, proper timing may act to save a life or prevent excessive myocardial damage. Further, various studies have associated arrhythmia with falls, for example, where an arrhythmia compromises blood flow to the brain or otherwise results in loss of body function (see, e.g., Mills et al., "Cardiac arrhythmia and hip fracture," *Int J Cardiol.*, 6(3):382–5 (1984)). In the case of a patient fitted with an implanted cardiac therapy device capable of delivering tiered anti-arrhythmia therapy, proper timing of a tier may act to reduce incidence of falls and/or lessen impact of a fall.

Conventional tiered therapy devices generally rely on timers or intracardiac electrograms to determine when to switch between therapy tiers. Hence, such conventional devices do not account for patient position, which may be related conscious state, risk of a fall, etc. As described herein, various exemplary devices, methods and/or systems determine patient position and/or patient movement and optionally use such information to determine when to switch between one tier and another. Various other exemplary devices, methods and/or systems are also disclosed, for example, to aid in detection of arrhythmic conditions.

SUMMARY

An exemplary method includes detecting movement of an in vivo oscillator using one or more in vivo sensors, receiving information from at least one of the one or more sensors, and deciding whether to switch an implanted cardiac therapy device from a lower tier of anti-arrhythmia therapy to a higher tier of anti-arrhythmia therapy based at least in part on the information. An exemplary implantable device includes a micro-electromechanical system (MEMS) capable of measuring acceleration and logic capable of determining postural sway based at least in part on acceleration measured by the MEMS. Various other exemplary methods, devices and systems are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators will be used to reference like parts or elements throughout.

Exemplary Stimulation Device

The techniques described below are intended to be implemented in connection with any stimulation device that is configured or configurable to stimulate nerves and/or stimulate and/or shock a patient's heart.

Figure 1:
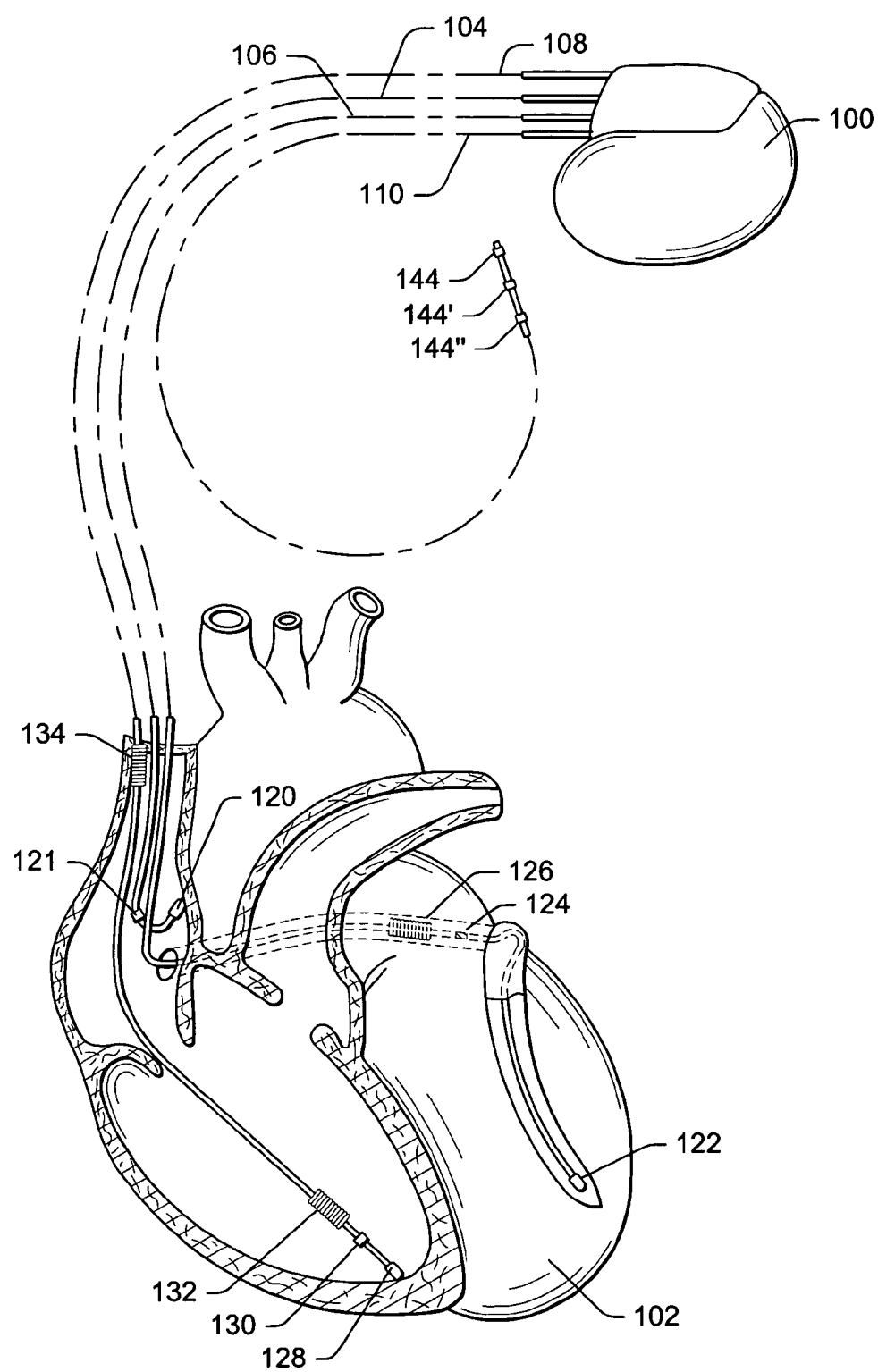
FIG. 1 is a simplified diagram illustrating an exemplary implantable stimulation device in electrical communication with at least three leads implanted into a patient's heart and at least one other lead for delivering stimulation and/or shock therapy. Exemplary devices may have lesser leads as well.

FIG. 1 shows an exemplary stimulation device 100 in electrical communication with a patient's heart 102 by way of three leads 104, 106, 108, suitable for delivering multichamber stimulation and shock therapy. The leads 104, 106, 108 are optionally configurable for delivery of stimulation pulses suitable for stimulation of autonomic nerves. In addition, the device 100 includes a fourth lead 110 having, in this implementation, three electrodes 144, 144', 144" suitable for stimulation of autonomic nerves, phrenic nerves and/or detection of other physiologic signals that may be used by the implanted system to modify the pacing parameters. This lead may be positioned in and/or near a patient's heart, near an autonomic nerve, or near a phrenic nerve within a patient's body and remote from the heart. The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which are incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve; such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve; such an electrode may be positioned on the lead or a bifurcation or leg of the lead.

Figure 2:
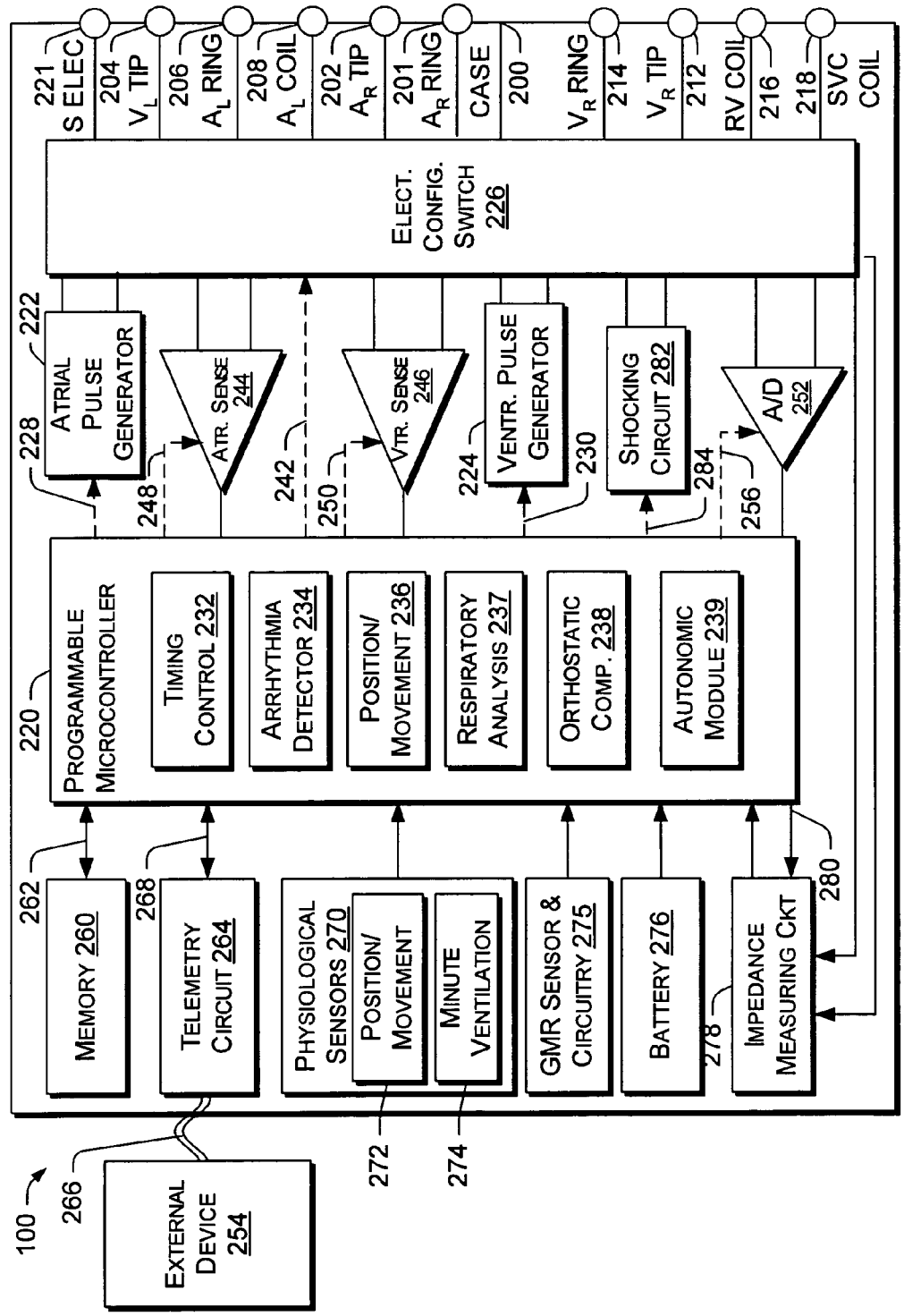
FIG. 2 is a functional block diagram of an exemplary implantable stimulation device illustrating basic elements that are configured to provide cardioversion, defibrillation, pacing stimulation and/or autonomic nerve stimulation or other tissue and/or nerve stimulation. The implantable stimulation device is further configured to measure position and/or movement.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal (AR TIP) 202 adapted for connection to the atrial tip electrode 120. A right atrial ring terminal (AR RING) 201 is also shown, which is adapted for connection to the atrial ring electrode 121. To achieve left chamber sensing, pacing, shocking, and/or autonomic stimulation, the connector includes at least a left ventricular tip terminal (VL TIP) 204, a left atrial ring terminal (AL RING) 206, and a left atrial shocking terminal (AL COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal (VR TIP) 212, a right ventricular ring terminal (VR RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander) and U.S. Pat. No. 4,944,298 (Sholder), all of which are incorporated by reference herein. For a more detailed description of the various timing intervals used within the stimulation device and their interrelationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, interatrial conduction (A—A) delay, or interventricular conduction (V—V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a position and/or movement analysis module 236 and optionally an orthostatic compensator 238 and a minute ventilation (MV) response module; the latter module is not shown in FIG. 2. These components can be utilized by the stimulation device 100 for determining desirable times to administer various therapies. The aforementioned components may be implemented in hardware as part of the microcontroller 220, or as software/firmware instructions programmed into the device and executed on the microcontroller 220 during certain modes of operation. Various exemplary methods described herein are optionally implemented as logic, which may be embodied in software and/or hardware.

Microcontroller 220 further includes a respiratory and/or autonomic characteristics analysis module 237. The respiratory and/or autonomic characteristics analysis module 237 optionally implements one or more methods for sensing, information analysis, and/or stimulation control. For example, the respiratory and/or autonomic characteristics analysis module 237 optionally implements one or more of the exemplary methods described below.

Microcontroller 220 further includes an autonomic nerve stimulation module 239 for performing a variety of tasks related to autonomic nerve stimulation. This component can be utilized by the stimulation device 100 for determining desirable times to administer various therapies, including, but not limited to, parasympathetic stimulation. The autonomic module 239 may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. Other features for arrhythmia detection, confirmation, etc. are discussed below and may be suitable as appropriate. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V—V Delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient.

In particular, the physiological sensors 270 include a position and/or movement sensor 272 mounted within the housing 200 of the stimulation device 100 to detect movement in the patient's position or the patient's position. Such a sensor may operate in conjunction with the position and/or movement analysis module 236. The position and/or movement sensor 272 may be implemented in many ways. In one particular implementation, the position sensor 272 is implemented as an accelerometer-based sensor capable of measuring acceleration, position, etc. For example, such a sensor may be capable of measuring dynamic acceleration and/or static acceleration. In general, movement of the patient will result in a signal from the accelerometer. For example, such an accelerometer-based sensor can provide a signal to the microcontroller 220 that can be processed to indicate that the patient is undergoing heightened physical exertion, moving directionally upwards or downwards, etc.

The physiological sensors 270 further include a minute ventilation (MV) sensor 274 to sense minute ventilation, which is defined as the total volume of air that moves in and out of a patient's lungs in a minute. The MV sensor 274 uses transthoracic impedance, which is a measure of impedance across the chest cavity. Lungs filled with air have higher impedance than empty lungs. Thus, upon inhalation, impedance increases; whereas upon exhalation, impedance decreases.

Signals generated by the position and/or movement sensor 272 and MV sensor 274 are optionally passed to the microcontroller 220 for analysis in determining whether to adjust the pacing rate, invoke the orthostatic compensator 238, and/or invoke the MV response module. The microcontroller 220 monitors the signals for indications of the patient's position and activity status, such as whether the patient is climbing upstairs or descending downstairs or whether the patient is sitting up after lying down.

More specifically, the microcontroller 220 receives a signal from the accelerometer-based sensor 272 that may be processed to produce an acceleration component along a vertical axis (i.e., z-axis signal). This acceleration component may be used to determine whether there is an increased or decreased level of activity in the patient, etc. The microcontroller 220 optionally integrates such a signal over time to produce a velocity component along the vertical direction. The vertical velocity may be used to determine a patient's position/activity aspects as well, such as whether the patient is going upstairs or downstairs. If the patient is going upstairs, the microcontroller 220 may increase the pacing rate or invoke the orthostatic compensator 238 to apply a prescribed pacing therapy, especially at the onset. If the patient is traversing downstairs, the device might decrease the pacing rate or perhaps invoke the MV response module to control pacing therapy during the descent. The MV response module determines a suitable pacing rate by, for example, measuring the transthoracic impedance from the MV sensor 274, computing the current MV, and comparing that with a long-term average of MV.

The microcontroller 220 can also monitor the sensor signals for any indication that the patient has moved from a supine position to a prone or upright position. For example, the integrated velocity signal computed from the vertical acceleration component of the sensor data may be used to determine that the patient has just stood up from a chair or sat up in bed. A sudden change in the vertical signal (e.g., a positive change in a direction normal to the surface of the earth), particularly following a prolonged period with little activity while the patient is sleeping or resting, confirms that a posture-changing event occurred. The microcontroller 220 optionally uses this information as one potential condition for deciding whether to invoke the orthostatic compensator 238 to apply cardiac pacing therapy for treating orthostatic hypotension. Other uses are described in more detail below.

While a two-axis accelerometer may adequately detect tilt with respect to acceleration of gravity, the exemplary stimulation device 100 may also or alternatively be equipped with a GMR (giant magnetoresistance) sensor and circuitry 275 that detects the earth's magnetic fields. The GMR sensor and circuitry 275 may be used to ascertain absolute orientation coordinates based on the earth's magnetic fields. The device is thus able to discern a true vertical direction regardless of the patient's position (i.e., whether the patient is lying down or standing up). Where three-axes are measured by various sensors, coordinates may then be taken relative to the absolute orientation coordinates from the GMR. For instance, as a person sits up, the axial coordinates of the accelerometer-based sensor 272 might change by 90°, but the sensor signals may be calibrated as to the true vertical direction based on the output of the GMR sensor and circuitry 275.

While shown as being included within the stimulation device 100, it is to be understood that the sensors and/or circuitry 272, 275 may also be external to the stimulation device 100, yet still be implanted within or carried by the patient and optionally capable of transmitting to and/or receiving information from the stimulation device 100.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

The impedance measuring circuit 278 may also measure impedance related to lung inflation. Such a circuit may use a case electrode, an electrode positioned in or proximate to the heart and/or another electrode positioned within the chest cavity. Various exemplary methods described below rely on impedance measurements to determine lung inflation and/or inspiratory vagal excitation, which can inhibit excitatory signals to various muscles (e.g., diaphragm, external intercoastals, etc.).

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Patient Position

During an ordinary day, a patient may assume supine, inclined, prone or other body positions. In some positions, risk of fall is non-existent; whereas, in other positions, a significant risk of fall exists. For example, a significant risk of fall exists for a free standing patient while a sleeping supine patient has little risk of fall.

To distinguish between the various patient positions, characteristics of these positions may be used. For example, various studies have shown that a prone and free standing human sways, primarily in the antero-posterior plane and secondarily in the medio-lateral plane (see, e.g., Morasso et al., "Computing the COM from the COP in postural sway movements,", *Human Movement Science*, 18:759–67 (1999)). A more formal definition defines sway as a persistent oscillation of the center of mass (COM) in the antero-posterior and medio-lateral planes. The center of mass (COM) can be considered a location where weight of a patient is concentrated and suitable for analyzing forces acting on the patient. Various techniques are available for determining center of mass (COM) including suspension techniques, moment subtraction techniques, segment techniques, etc. For most patients, center of mass (COM) lies at a location at or below the navel.

Another characteristic of a prone, free standing position is maximum recoverable angle of lean. A study by Owings et al., "Maximum recoverable angle of lean does not differ between older men and women", American Society of Biomechanics, 25th Annual Meeting, San Diego, Calif., 2001, demonstrated that an angle of approximately 15 degrees corresponds to an average maximum recoverable angle of lean. For example, an average patient cannot recover from an angle of lean greater than the maximum recoverable angle of lean and hence, for a patient having such an angle of lean, a fall is highly likely and imminent.

Other studies have examined frequency components of sway to determine risk of fall (see, e.g., Lee et al., "Prediction of fall risk in the elderly: Time-dependent measures of postural sway dynamics", Poster Session (0806), 47th Annual Meeting, Orthopaedic Research Society, Feb. 25–28, 2001, San Francisco, Calif.). The study by Lee et al. examined time rate of change in a frequency component of sway (3 Hz sway component over 80 seconds) and found that this component decreases in normal and young while it remains flat or increases in elderly or those having a higher risk of falling.

As described herein, one or more sensors sense parameters related to patient position and/or patient movement. Various exemplary devices, methods and/or systems optionally use such parameters to determine risk of a patient falling, patient falling, patient stability/instability, patient position, patient movement, when to switch a patient's therapy, whether a patient has a particular cardiac condition, etc.

Figure 3:
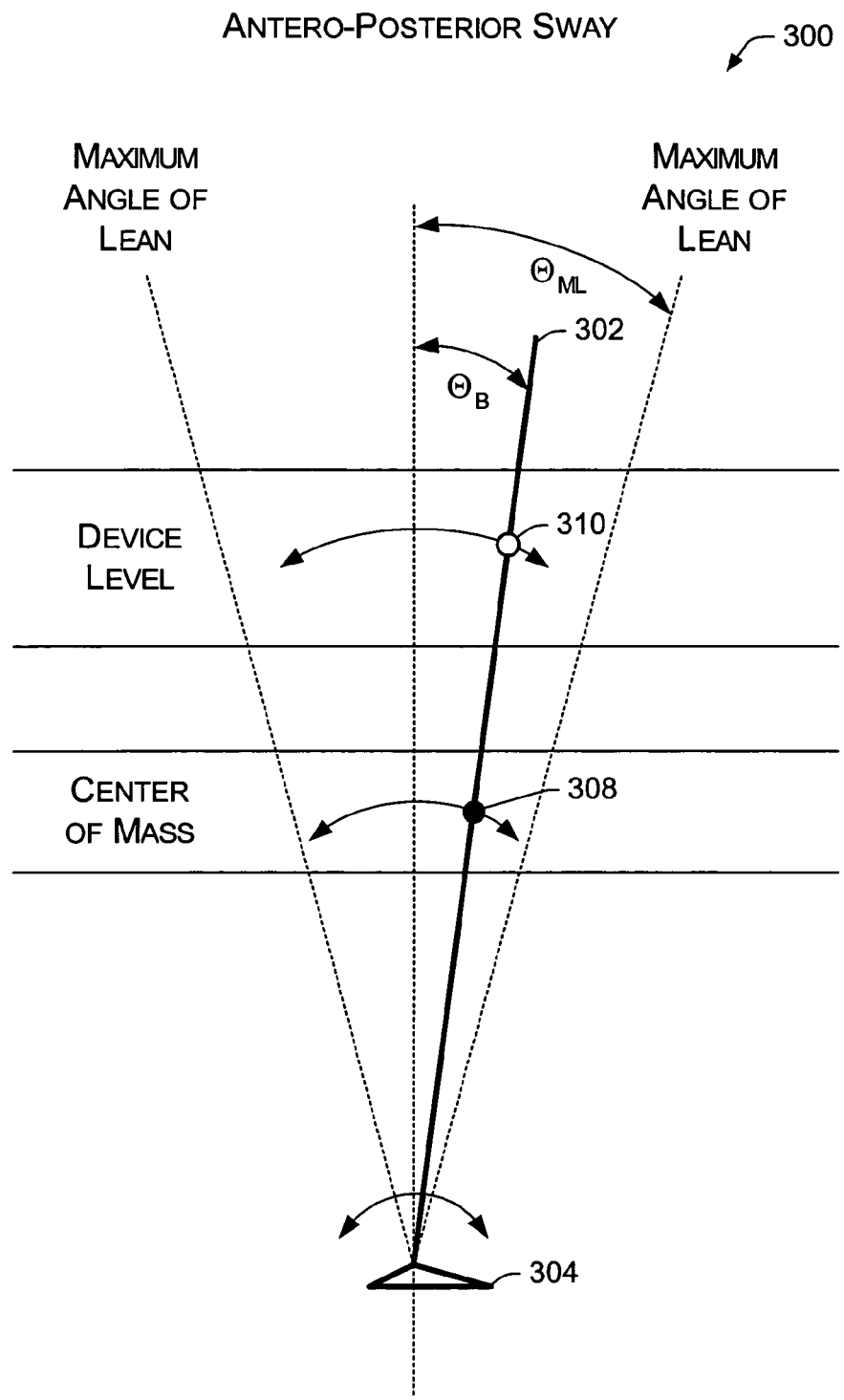
FIG. 3 is an approximate anatomical diagram of a patient experiencing postural sway (e.g., in an antero-posterior plane).

FIG. 3 shows a diagram of antero-posterio sway 300. A patient 302 sways in an antero-posterior z-x plane about a base 304 (e.g., the patient's ankles/feet). The patient 302 forms an angle $\Theta_B$ with a central z-axis and $\Theta_{ML}$, represents a maximum angle of lean from the z-axis. The patient 302 has a device 310 implanted at a relatively fixed location. For the standing patient 302, the implanted device 310 resides at some device level during sway. A center of mass (COM) 308 resides at a lower level. Note that for a given angle of sway, the center of mass (COM) 308 exhibits less movement than the implanted device 310. Thus, various exemplary methods include implanting a device in a patient at a higher z-axis location than the patient's center of mass (COM). Such exemplary methods allow an implanted device to experience greater displacement and acceleration compared to a device implanted at the center of mass (COM). However, as described below, a satellite or slave device may be optionally implanted closer to a patient's center of mass (COM). Such an alternative can allow for additional position and/or movement determinations.

Figure 4:
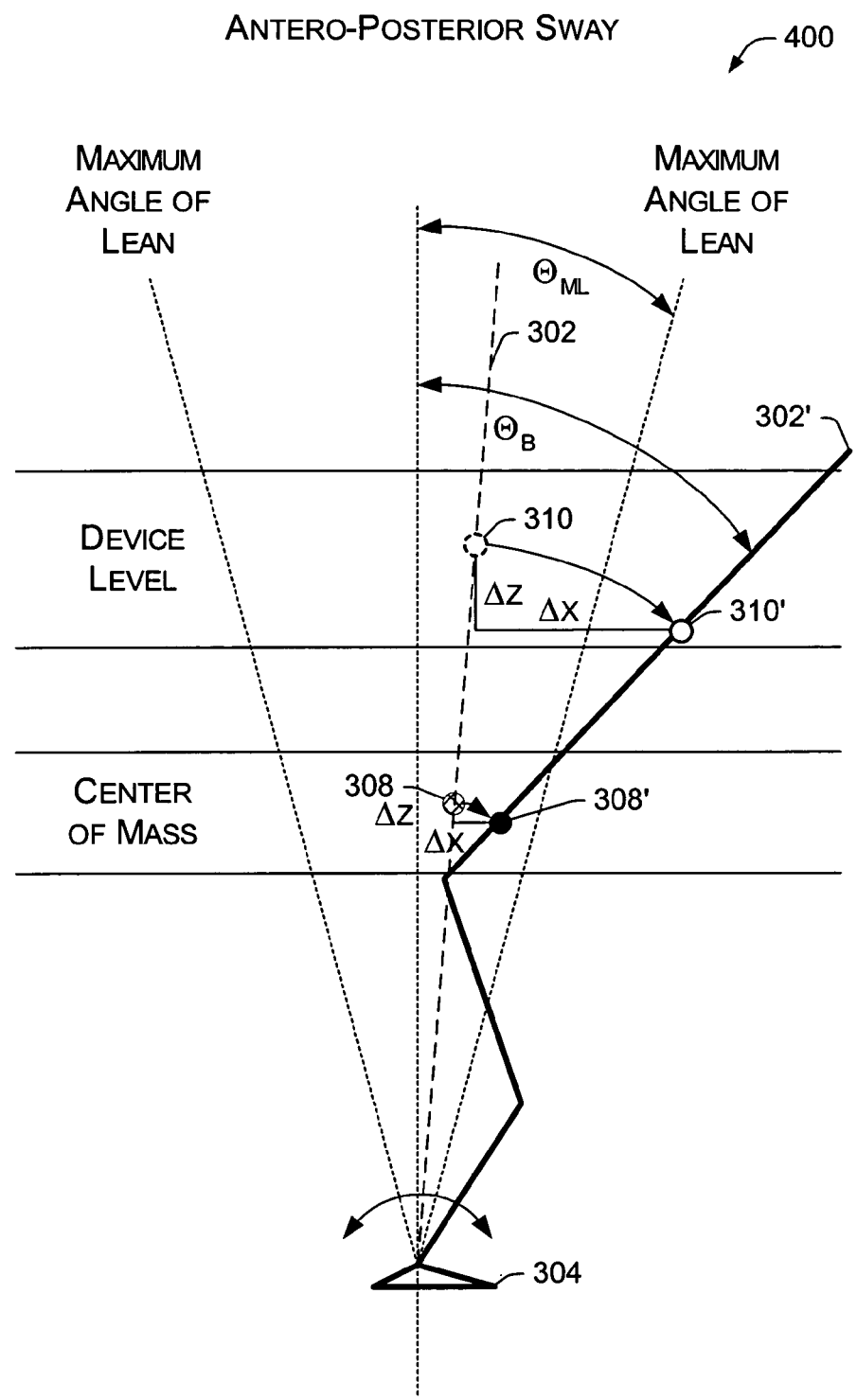
FIG. 4 is an approximate anatomical diagram of a patient experiencing instability such as that associated with a fall.

FIG. 4 shows a diagram of antero-posterio sway 400 that corresponds to a patient 302 falling. In this example, the patient 302 has bent at the knees and the hips and the patient's upper body has moved past the maximum angle of lean $\Theta_{ML}$ to a new patient position 302'. Such falling may have been initiated by a sway past the maximum angle of lean, a collapse in the knees, etc. As a result of the falling, the implanted device 310 has moved to a new device position 310' and the center of mass (COM) 308 has moved to a new COM position 308'. In so doing, the implanted device 310 moved some distance $\Delta z$ along the z-axis and some distance $\Delta x$ along the x-axis and the center of mass (COM) moved some distance $\Delta z$ along the z-axis and some distance $\Delta x$ along the x-axis. In this example, for the implanted device 310 $\Delta z$ and $\Delta x$ are greater than $\Delta z$ and $\Delta x$ of the center of mass (COM) 308.

Figure 5:
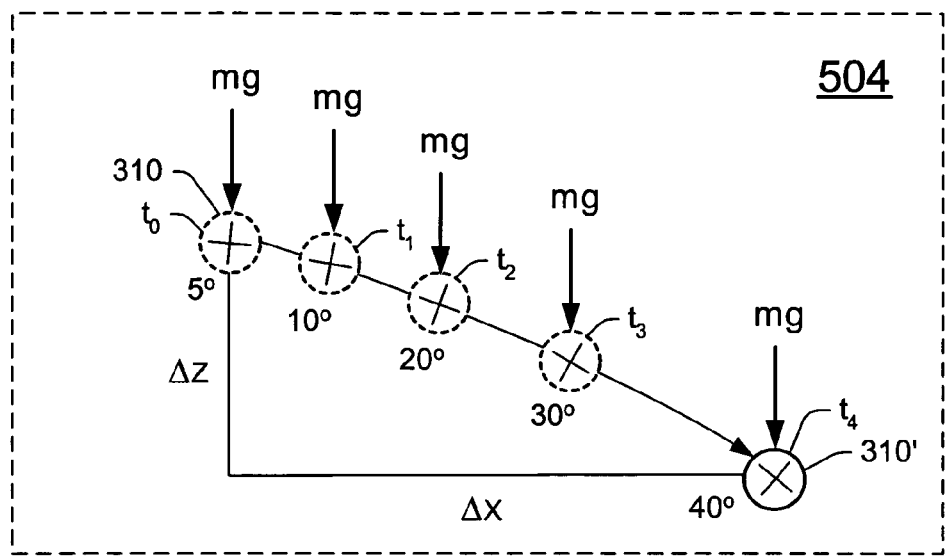
FIG. 5 is a plot of device movement, an exemplary sensor for the device, and exemplary equations for dynamic and static acceleration.
Figure 5:
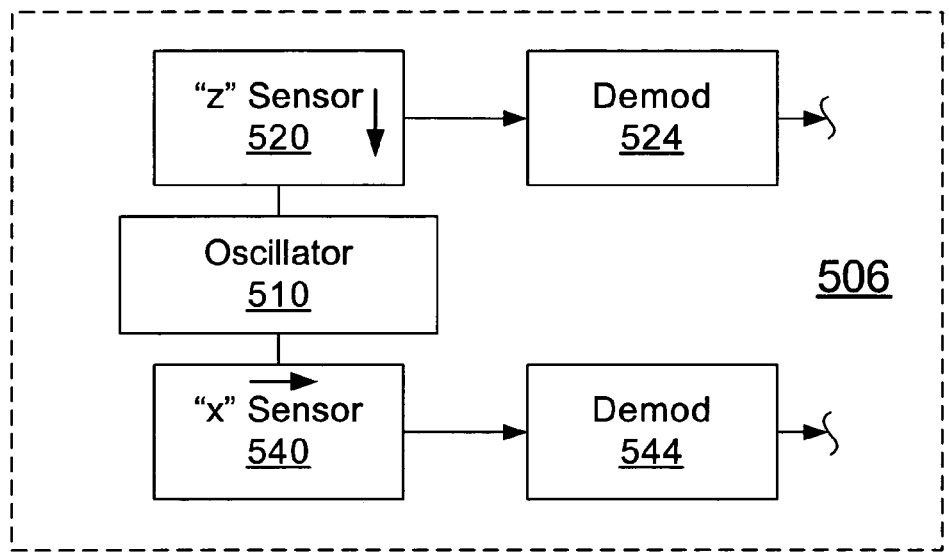

FIG. 5 shows a detailed time incremental diagram 504 of the implanted device 310, progressing to the implanted device position 310' wherein the time increments are assumed equal. In this example, the device 310 starts at an initial time $t_0$ and an angle with respect to the acceleration of gravity of approximately 5°. At a time $t_1$, the device 310 has moved in both x and z directions and its angle with respect to gravity has increased to approximately 10°. At a time $t_2$, the device 310 has experienced an increase in velocity and its angle with respect to gravity, approximately 20°. At a time $t_3$, the device 310 has experienced a further increase in velocity due at least in part to the acceleration of gravity, which now forms an angle of approximately 30° with the device 310. At a time $t_4$, the device position 310' corresponds to an angle with respect to gravity of approximately 40° and displacements of $\Delta z$ and $\Delta x$ from the device position at $t_0$.

An exemplary circuit 506 capable of measuring various aforementioned position and/or movement parameters includes an oscillator 510, a "z" sensor 520 coupled to the oscillator 510 and a "x" sensor 540 coupled to the oscillator 510. Thus, each of the sensors has a predominant axis for sensing, which is optionally orientable with respect to one or more other sensors, acceleration of gravity, a patient, the ground, etc. According to this exemplary circuit 506, the sensors 520, 540 respond to movement of the oscillator 510 and communicate information to other components for further processing, for example, a "z" sensor demodulator 524 and an "x" sensor demodulator 544. Demodulated signals may be further communicated as required. As described herein, the oscillator 510, the "z" sensor 520 and the "x" sensor 540 are typically positioned in vivo, for example, an in vivo oscillator and one or more in vivo sensors.

The exemplary circuit 506 or system is sometimes referred to as a dual axis accelerometer. Such a circuit may measure dynamic and/or static acceleration. Measurement of static acceleration allows a circuit to serve as a tilt sensor wherein tilt corresponds to an angle with respect to earth's gravitational acceleration. For example, consider the commercially available micro-electromechanical system (MEMS) marketed as the ADXL202 by Analog Devices, Inc. (Norwood, Mass.), which has a mass of about 5 grams and a 14 lead CERPAK (approx. 10 mm by 10 mm by 5 mm or a volume of approx. 500 mm). The ADXL202 MEMS is a dual-axis accelerometer on a single monolithic integrated circuit and includes polysilicon springs that provide a resistance against acceleration forces. The ADXL202 MEMS is capable of measuring tilt. The term MEMS has been defined generally as a system or device having micro-circuitry on a tiny silicon chip into which some mechanical device such as a mirror or a sensor has been manufactured. The aforementioned ADXL202 MEMS includes micro-circuitry and a mechanical oscillator.

In principle, an accelerometer can use the force of gravity as an input vector to determine orientation of an object in space. Further, an accelerometer is typically most sensitive to tilt when its sensitive axis is perpendicular to the force of gravity (i.e., parallel to the earth's surface). For example, when an accelerometer is oriented on axis to gravity (i.e., near its +1 g or −1 g reading), the change in output acceleration per degree of tilt is negligible. However, when an accelerometer is perpendicular to gravity, its output will change nearly 17.5 mg per degree of tilt, but at 45° degrees it is changing only at 12.2 mg per degree and resolution declines. Various exemplary methods, devices and/or systems disclosed herein include an implantable device with an accelerometer having at least one axis sensor oriented substantially perpendicular to the acceleration of earth's gravity when implanted in a patient. As noted above, Owings et al. found an average maximum recoverable angle of lean or tilt of approximately 15°, with respect to the acceleration of gravity. Thus, such a perpendicular orientation of a sensor axis allows for increased sensitivity to sway and lean or tilt when compared to other orientations (e.g., normal to the acceleration of gravity).

An exemplary dual axis accelerometer may also be oriented so both of its axes are parallel to the earth's surface. In such an example, the accelerometer can be used as a two axis tilt sensor with a roll and a pitch axis. In this example, once an output signal from the accelerometer has been converted to an acceleration (e.g., $a_1$ and $a_2$) that varies between −1 g and +1 g, the output tilt in degrees may be calculated as follows: pitch=asin ($a_1$/1 g); roll=asin ($a_2$/1 g).

Compensation may be made for other acceleration, for example, a patient in an elevator, an automobile, etc. FIG. 5 also shows some exemplary equations and/or variables 508 for dynamic acceleration and static acceleration.

Various exemplary methods, devices and/or systems optionally use one or more accelerometers and/or accelerometers having one or more axes, for example, orientable in a substantially orthogonal manner (e.g., x, y and z directions). A position and/or movement sensor, whether or not accelerometer-based, may optionally operate in a cylindrical coordinate system and/or another coordinate system. While various examples mention orientation with respect to acceleration of gravity or earth's surface, other orientations may be used. Further, various exemplary methods, devices and/or systems may optionally use a first dual-axis accelerometer and a second dual-axis accelerometer wherein the two axes of the first dual-axis accelerometer define a first plane and the two axes of the second dual-axis accelerometer define a second plane and wherein the first plane differs from the second plane.

Figure 6:
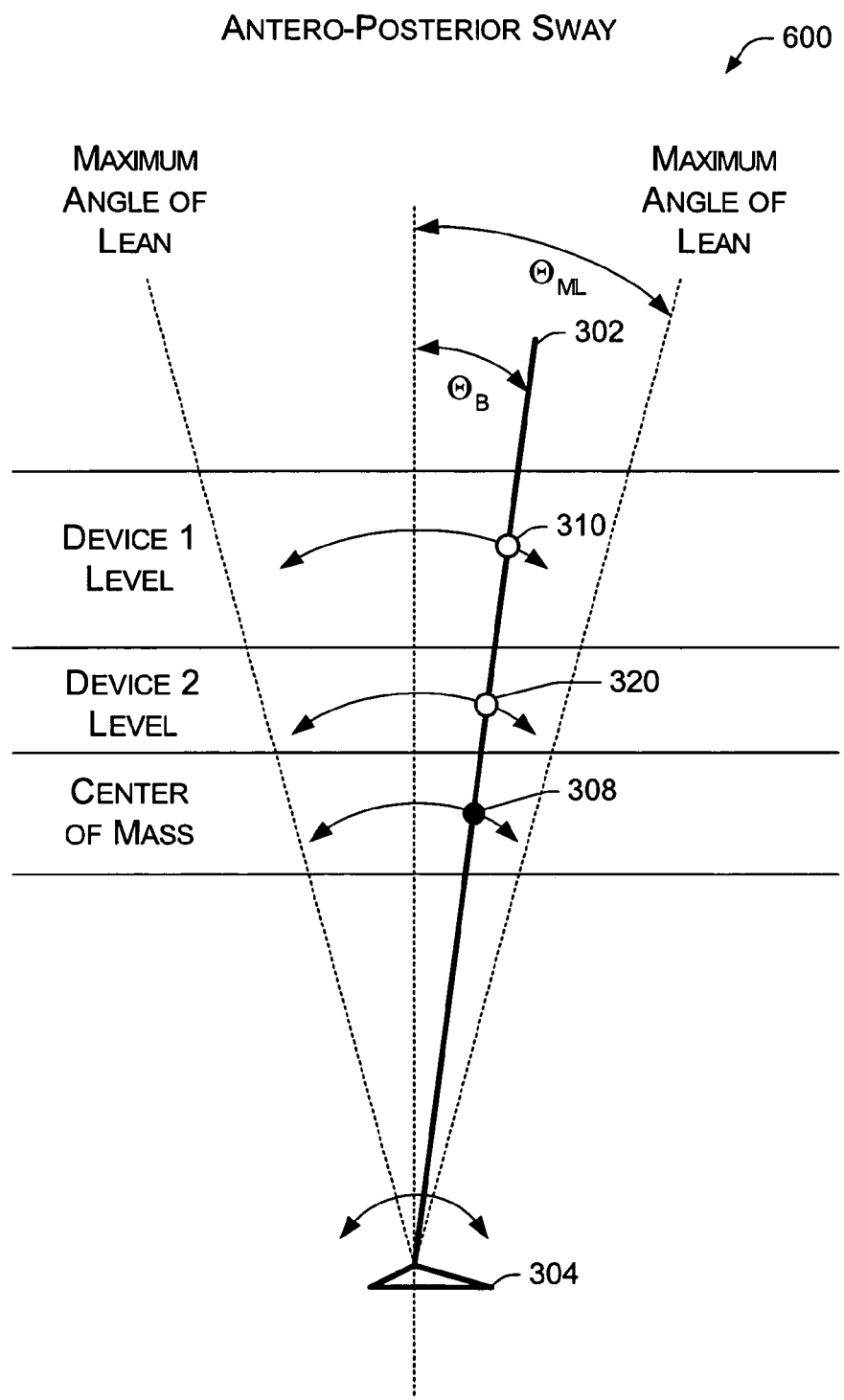
FIG. 6 is an approximate anatomical diagram of a patient having two devices wherein at least one device has position and/or movement sensing capabilities.

FIG. 6 shows an exemplary system 600 that includes more than one position and/or movement sensing device. In this example, a body 302 has a first device 310 positioned at one location and a second device 320 positioned at another location. The first device 310 and the second device 320 may be capable of transmitting and/or receiving information. For example, the second device 320 may communicate with the first device 310. In the exemplary system 600, the second device 320 is optionally positioned in the front lower abdominal region. Implantation at this location may have minimal discomfort due to the soft underlying intestines. Communication between the two devices may occur via radio frequency (RF) telemetry or by Galvanic signaling (e.g., direct stimulation of body tissue by one device and direct reception by one or more electrodes integral with, on, or in electrical contact with another device wherein the one or more electrodes and/or other device are in contact with body tissue as well).

Exemplary Methods

Figure 7:
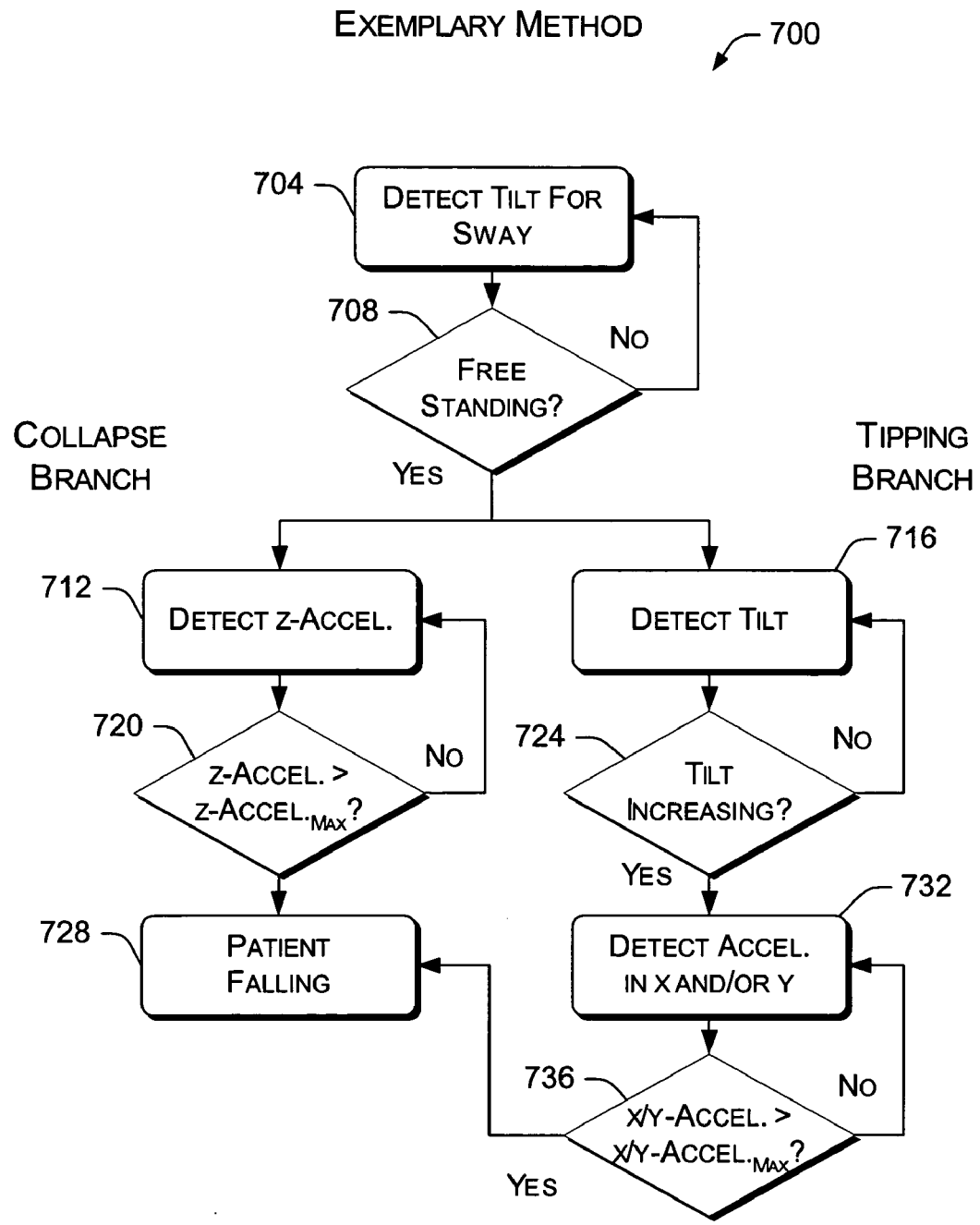
FIG. 7 is a block diagram of an exemplary method for monitoring patient position and/or movement.

FIG. 7 shows an exemplary method 700 for determining if a patient is substantially free standing and/or falling. In a detect block 704, detection of tilt is used as an indicator for postural sway. Based at least in part on such information, a decision block 708 decides whether a patient is free standing. If the decision block 708 decides that the patient is not free standing, the exemplary method 700 returns to the detect block 704. However, if the decision block 708 decides that the patient is free standing, then the method 700 detects z-acceleration in a z-acceleration detect block 712 and detects tilt in another tilt detection block 716.

The z-acceleration block 712 may be associated with a "collapse" branch of such an exemplary method while the tilt detection block 716 may be associated with a "tipping" branch of such an exemplary method. In this example, the collapse branch uses movement in the z-direction, substantially normal to gravitational acceleration, as an indicator of a patient collapsing; whereas, the tipping branch uses movement in an angle substantially aligned to gravitation acceleration as an indicator of a patient tipping (e.g., about a base such as the feet).

A decision block 720 follows the z-acceleration detect block 712 that decides if the z-acceleration has exceeded some predetermined z-acceleration (e.g., z-accel.$_{Max}$). If the decision block 720 decides that the z-acceleration does not exceed a predetermined value, then the method 700 continues at the z-acceleration detection block 712. If the decision block 720 decides that the z-acceleration does exceed a predetermined value, then the method 700 concludes that the patient is falling (see, e.g., the patient falling block 728).

A decision block 724 follows the tilt detection block 716 that decides whether tilt is increasing, for example, according to one or more criteria (e.g., a predetermined angle of tilt or lean, a predetermined rate, a predetermined period of time, etc.). If the decision block 724 decides that the tilt is increasing accordingly, then the exemplary method 700 continues in an x- and/or y-acceleration detection block 732. Otherwise, the method 700 continues in the tilt detection block 716. Another decision block 736 follows the x- and/or y-acceleration detection block 732 that decides if the x- and/or y-acceleration exceed some predetermined value or values. If the decision block 732 decides that such accelerations are within limit (e.g., established by the value or values), then the method 700 may continue at the acceleration detection block 732 or at the detection block 716. However, if the x- and/or y-acceleration exceed the predetermined value or values, then the method 700 continues in the patient falling block 728 to indicate that the patient is falling.

While the exemplary method 700 shows two separate branches, other exemplary methods optionally use any of the information detected in each of these branches to determine a patient's position, stability or instability. As described herein, such exemplary methods are optionally used to determine when to switch from one tier of therapy to another and/or to determine or confirm a particular cardiac condition.

Figure 8:
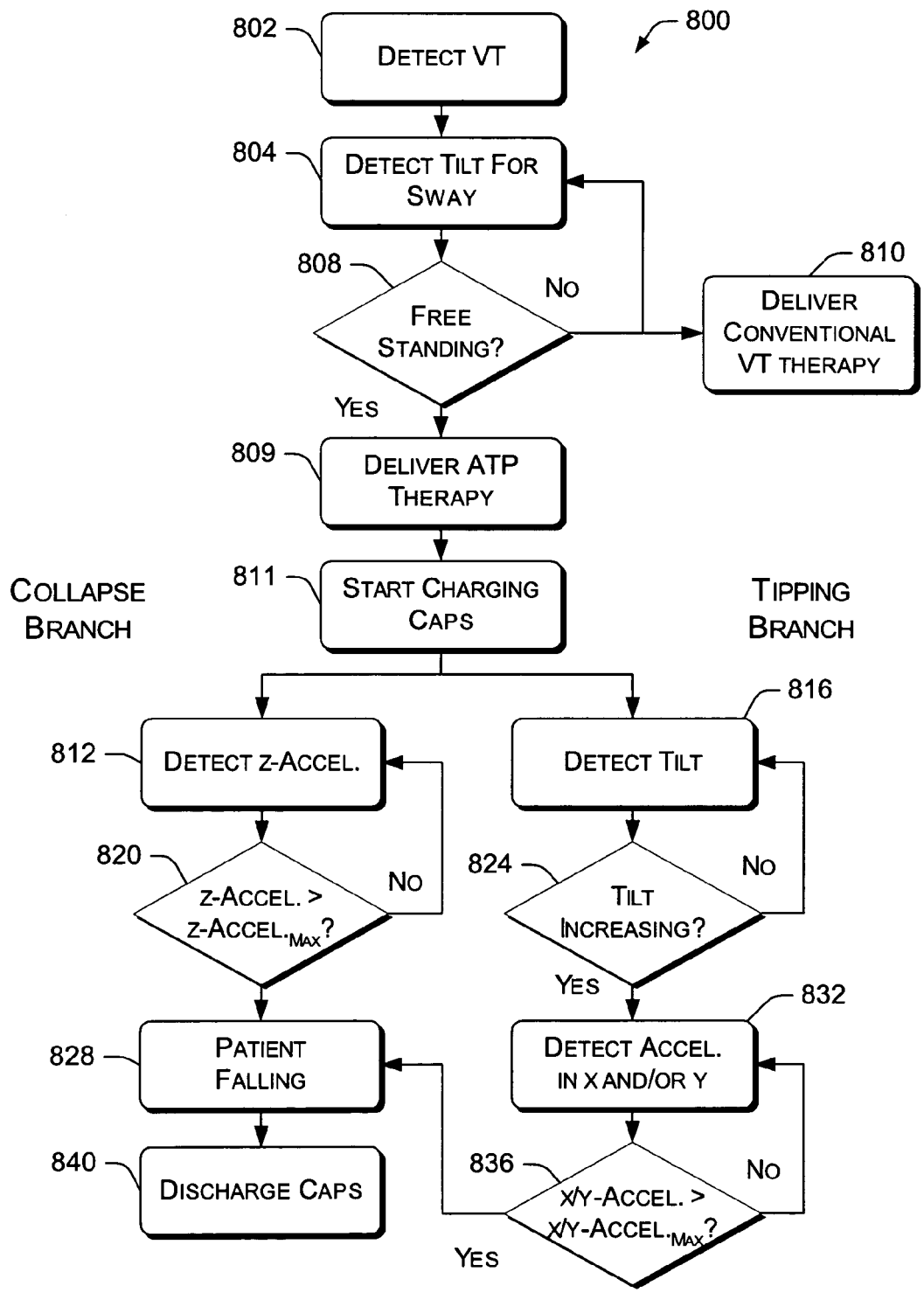
FIG. 8 is a block diagram of an exemplary method for monitoring patient position and/or movement and optionally using such information to delivery cardiac therapy.

FIG. 8 shows an exemplary method 800 for switching from one tier of therapy to another. Such an exemplary method may further prepare for a particular tier of therapy based on information related to a patient's position, stability or instability. In a detection block 802, a ventricular tachycardia is detected. Such a cardiac condition may worsen or improve. At some point in time, an implanted cardiac therapy device may, in response to detection of a ventricular tachycardia, deliver therapy in an effort to improve a patient's condition. Various tiered therapy approaches include those that implement anti-tachycardia pacing therapy prior to one or more forms of cardioversion or defibrillation shock therapy.

According to the exemplary method 800, a tilt detection block 804 follows detection of the ventricular tachycardia. Detection of tilt is used as an indicator for postural sway or other criterion that may indicate that a patient is free standing. Based at least in part on such information, a decision block 808 decides whether a patient is free standing. If the decision block 808 decides that the patient is not free standing, the exemplary method 800 returns to the detect block 804 and, in a delivery block 810, commences, for example, conventional therapy for treating the ventricular tachycardia. However, if the decision block 808 decides that the patient is free standing, then, in another delivery block 809, the method 800 commences delivery of an anti-tachycardia therapy as a tier of tiered therapy that includes one or more forms of cardioversion or defibrillation shock therapy in a higher therapy tier.

In general, such shock therapies rely on charging one or more special purpose capacitors or other charge storage units. For example, commercially available implantable defibrillation devices typically include at least two capacitors. In such devices, the capacitors are typically charged to approximately 800V in series. These capacitors have a relatively high capacitance and relatively small dimensions and hence volume (e.g., two capacitors may occupy about 8 cubic centimeters). A commercially available implantable defibrillation device may include two 400 volt, 188 microfarad ($\mu F$) capacitors connected in series to form an equivalent 800 V, 94 $\mu F$ capacitor. This is capable of producing a short pulse of approximately 30 joules and approximately 10 milliseconds in duration. Charge time to achieve a full charge for such a two capacitor charge storage unit may vary from approximately 5 to approximately 15 seconds, depending on various factors such as stored charge, battery strength, battery output, etc.

According to the exemplary method 800, a start charging block 811 follows the decision block 808. In this example, charging commences earlier than in a conventional tiered therapy because the patient is standing, which typically corresponds to a risk of falling. As described below, early charging may allow for earlier delivery of a shock, which, in turn, may help prevent or lessen severity of a fall. In particular, falls associated with a lack of blood flow to the brain may be prevented by early delivery of a shock. In the exemplary method 800, early delivery corresponds to delivery at a time of some determined degree of patient instability, which may proceed a fall or be an initial indication of falling.

The exemplary method 800 optionally includes a collapse branch and a tipping branch wherein a z-acceleration block 812 may be associated with a "collapse" branch while a tilt detection block 816 may be associated with a "tipping" branch. In this example, the collapse branch uses movement in the z-direction, substantially normal to gravitational acceleration, as an indicator of a patient collapsing; whereas, the tipping branch uses movement in an angle substantially aligned to gravitation acceleration as an indicator of a patient tipping (e.g., about a base such as the feet).

A decision block 820 follows the z-acceleration detect block 812 that decides if the z-acceleration has exceeded some predetermined z-acceleration (e.g., z-accel.$_{Max}$). If the decision block 820 decides that the z-acceleration does not exceed a predetermined value, then the method 800 continues at the z-acceleration detection block 812. If the decision block 820 decides that the z-acceleration does exceed a predetermined value, then the method 800 concludes that the patient is falling (see, e.g., the patient falling block 828). Thereafter, the method 800 proceeds to a discharge block 840, wherein a shock is delivered in an effort to promote blood flow.

A decision block 824 follows the tilt detection block 816 that decides whether tilt is increasing, for example, according to one or more criteria (e.g., a predetermined angle of tilt or lean, a predetermined rate, a predetermined period of time, etc.). If the decision block 824 decides that the tilt is increasing accordingly, then the exemplary method 800 continues in an x- and/or y-acceleration detection block 832. Otherwise, the method 800 continues in the tilt detection block 816. Another decision block 836 follows the x- and/or y-acceleration detection block 832 that decides if the x- and/or y-acceleration exceed some predetermined value or values. If the decision block 832 decides that such accelerations are within limit (e.g., established by the value or values), then the method 800 may continue at the acceleration detection block 832 or at the detection block 816. However, if the x- and/or y-acceleration exceed the predetermined value or values, then the method 800 continues in the patient falling block 828 to indicate that the patient is falling. Thereafter, the method 800 proceeds to the discharge block 840, wherein a shock is delivered in an effort to promote blood flow.

While the exemplary method 800 shows two separate branches, other exemplary methods optionally use any of the information detected in each of these branches to determine a patient's position, stability or instability and/or to determine when to charge a charge storage, switch tiers of therapy, deliver a shock, etc. As described herein, such exemplary methods are optionally used to determine or confirm a particular cardiac condition.

Figure 9:
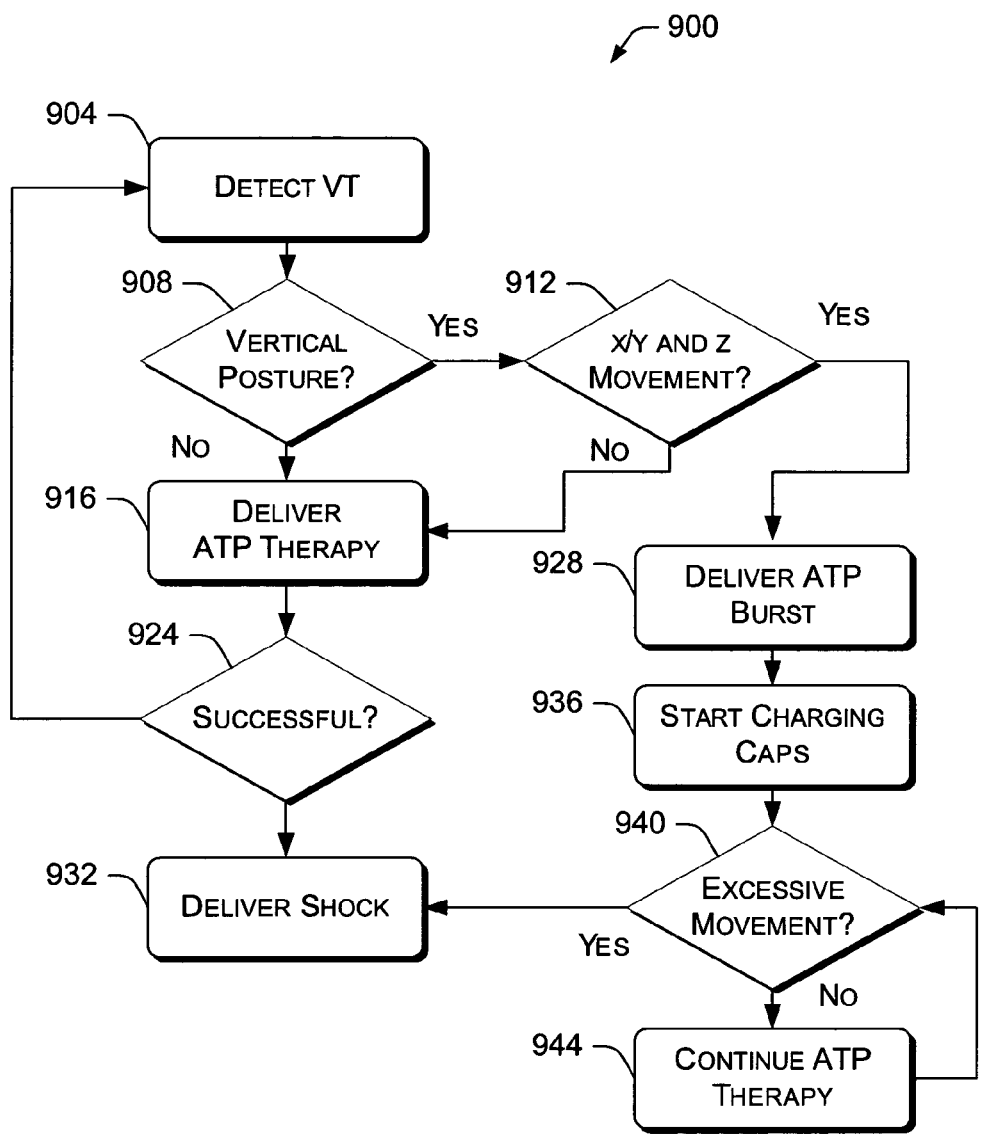
FIG. 9 is a block diagram of an exemplary method for monitoring patient position and/or movement and optionally using such information to delivery cardiac therapy.

FIG. 9 shows an exemplary method 900 for using patient position and/or patient movement in tiered anti-arrhythmia therapy. In a detect block 904, a ventricular tachycardia is detected in a patient. Following detection, a decision block 908 decides if the patient has a substantially vertical posture. A substantially vertical posture (e.g., less than approximately 15 degrees of lean or tilt) typically indicates that the patient is standing or otherwise at risk of falling. If the decision block 908 decides that the patient does not have a vertical posture, then in a delivery block 916, delivery of an anti-tachycardia pacing (ATP) therapy occurs. Another decision block 924 follows that determines if the ATP therapy was successful. If the decision block 924 determines that the ATP therapy was successful, then the exemplary method 900 returns to the detection block 904 or a monitoring block as appropriate. However, if the ATP therapy does not succeed in terminating the arrhythmic condition (e.g., the ventricular tachycardia, etc.), then the method 900 continues in another delivery block 932, which delivers a higher tier of anti-arrhythmia therapy, which, in this instance, includes delivery of a shock.

Referring again to the decision block 908, if this block decides that the patient has a vertical posture, then the exemplary method 900 continues in another decision block 912 that decides if the patient exhibits any significant movement, for example, in x, y and/or z directions. Such a decision may be based on information received from one or more accelerometers and/or other position and/or movement sensors. If the decision block 912 decides that the patient has no significant movement, then the method 900 continues in the delivery block 916, which delivers ATP therapy. In this instance, while the patient may have a vertical posture, the patient may be leaning against a wall, holding onto something, sitting in chair, etc.; thus, there may be less risk of a free fall. However, if the decision block 912 decides that there is significant movement (e.g., indicative of free standing), then the method 900 concludes that the patient is free standing and continues in a delivery block 928, which delivers an immediate burst of anti-tachycardia pacing (ATP) therapy. In a start charging block 936, the method 900 also commences charging one or more capacitors or a charge storage capable of participating in delivery of a shock. Both the ATP block 928 and the start charging block 936 act to expedite delivery of therapy aimed at minimizing risk of fall that may be associated with the arrhythmic condition.

The method 900 continues in yet another decision block 940 that decides if the patient exhibits excessive movement and/or change in position. If patient movement and/or position do not change in any significant manner, which may be indicative of a fall or a heightened risk of fall, then the method 900 continues delivery of ATP therapy in a continuation block 944. However, if a significant change occurs, then the method 900 enters a shock delivery block 932, which delivers a shock that aims to increase blood flow and/or terminate any arrhythmic condition.

While the exemplary method 900 shows commencement of charging only after deciding that the patient is free standing, charging may commence at an early time, for example, after the method 900 decides that the patient has a substantially vertical posture. Various exemplary methods, devices and/or systems optionally collect a patient history or assess a patient's risk of falling and then determine when to commence charging based at least in part on such information. For example, the study of Lee et al. discloses an 80 second, 3 Hz analysis that can help determine risk of fall for a patient. Thus, if such an analysis indicates that a patient has an increased risk of fall, then charging may commence at an early stage. While one aspect of the exemplary method 900 concerns charging, another aspect concerns shock delivery. In general, these two aspects are related where a sufficient charge does not exist prior to detection of the arrhythmia. In instances where charge storage has a sufficient charge prior to detection of arrhythmia, then position and/or movement information may be used to control shock delivery alone. Another aspect of the exemplary method 900 abandons a lower tier of therapy, typically to start implementation of a higher tier of anti-arrhythmia therapy.

Figure 10:
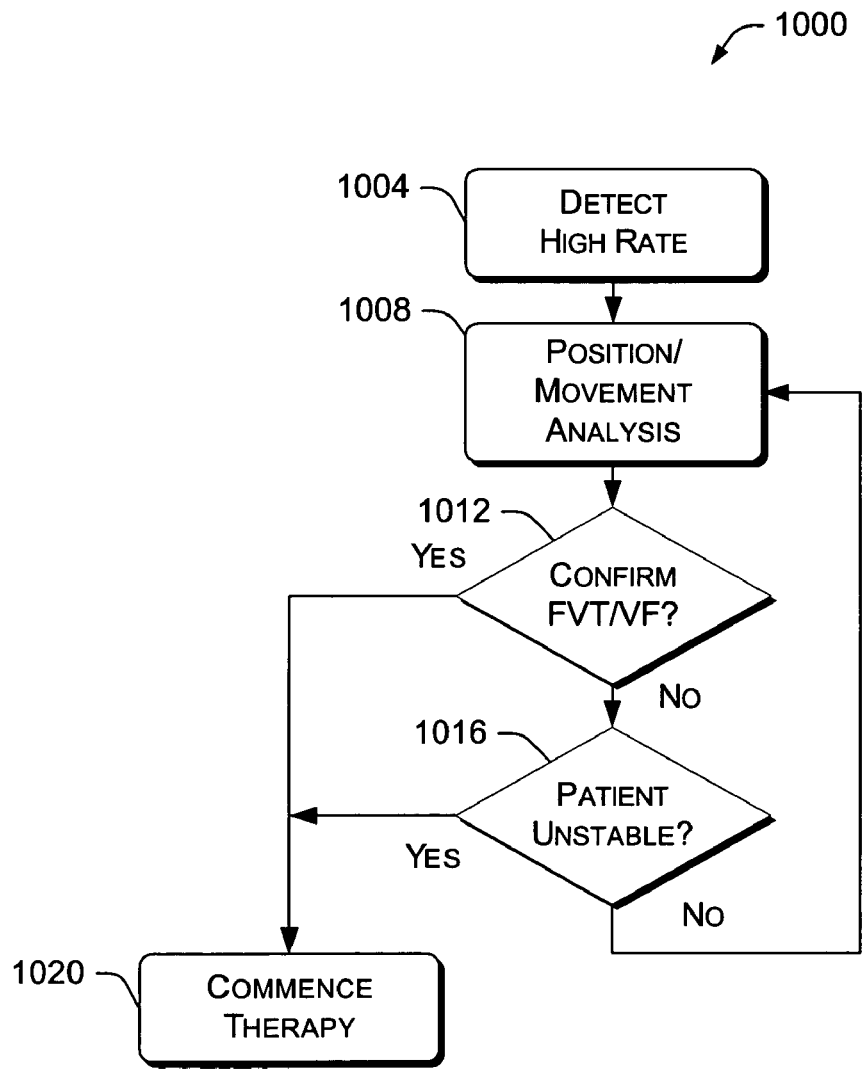
FIG. 10 is a block diagram of an exemplary method for monitoring patient position and/or movement and optionally using such information to determine or detect a cardiac condition.

As already mentioned, position and/or movement information may aid in detecting fast ventricular tachycardia and/or ventricular fibrillation. A fast ventricular tachycardia typically has a rate greater than approximately 200 beats per minute (bpm). FIG. 10 shows an exemplary method 1000 that includes confirming an arrhythmic condition based at least in part on patient position and/or movement. For example, if a conventional confirmation algorithm fails to confirm the presence of a particular arrhythmia, then patient position and/or movement may serve as a surrogate, especially if the patient experiences a decrease in blood flow that causes instability, which may include a fall.

In a detect block 1004, the exemplary method 1000 detects a high heart rate, for example, a high ventricular rate wherein a set number of fast beats occur back-to-back or within some beat or time interval (e.g., three fast beats back-to-back, four fast beats in a 2 second time interval, etc.). A fast beat, for example, may be a beat having a corresponding rate above some baseline for a particular patient. Such a rate is optionally predetermined, for example, by a care provider and/or by a method operating in an implanted device. Such a corresponding rate may be below that of a fast ventricular tachycardia. After detection of a high rate, the method 1000 continues in a position and/or a movement analysis block 1008, for example, wherein patient position and/or movement are monitored. The method 1000 continues in a decision block 1012 that decides whether the detected high rate per block 1004 corresponds to fast ventricular tachycardia or ventricular fibrillation. If the decision block 1012 decides that the patient has fast ventricular tachycardia or ventricular fibrillation, then the method 1000 commences an appropriate anti-arrhythmia therapy per the therapy block 1020. However, if the decision block 1012 decides that the detected fast rate does not correspond to fast ventricular tachycardia or ventricular fibrillation, then in another decision block 1016, the method 1000 decides whether the patient is unstable or experiencing instability such as a fall. If the decision block 1016 decides that the patient is unstable or experiencing instability (e.g., postural instability), then the method 1000 continues in the therapy block 1020. Otherwise, the method 1000 continues in the position and/or movement analysis block 1008.

According to the exemplary method 1000, detection of an unstable patient or a patient instability may indicate that the patient has inadequate blood flow, for example, to the brain. On the basis of patient history, type of arrhythmia, etc., such indication may be related to a potentially serious cardiac condition.

CONCLUSION

Although exemplary methods, systems and/or devices have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices and/or systems.

What is claimed is:

1. A method comprising:
  detecting movement of an in vivo oscillator using one or more in vivo sensors, the one or more in vivo sensors being a micro-electromechanical system (MEMS) capable of measuring acceleration, the MEMS having a first dual-axis accelerometer and a second dual-axis accelerometer, the two axes of the first dual-axis accelerometer defining a first plane and the two axes of the second dual-axis accelerometer defining a second plane, and the first plane differing from the second plane;
  receiving information from at least one of the one or more sensors; and
  deciding whether to switch an implanted cardiac therapy device from a lower tier of anti-arrhythmia therapy to a higher tier of anti-arrhythmia therapy based at least in part on the information;
  wherein the deciding includes determining whether the received information indicates that a patient has exceeded a predetermined acceleration; and
  wherein the predetermined acceleration has a substantial component aligned with the acceleration of earth's gravity.

2. The method of claim 1, wherein the detecting includes two in vivo sensors wherein each sensor has a predominant axis and the predominant axes of the sensors are oriented orthogonally.

3. The method of claim 1, wherein the deciding includes determining whether the received information indicates that a patient has exceeded a maximum recoverable angle of lean.

4. The method of claim 1, wherein the lower tier of anti-arrhythmia therapy is anti-tachycardia pacing therapy.

5. The method of claim 1, wherein the higher tier of anti-arrhythmia therapy is shock therapy.

6. The method of claim 1, wherein the higher tier corresponds to defibrillation shock therapy.

7. The method of claim 6, wherein the lower tier corresponds to anti-tachycardia pacing therapy.

8. A method comprising:
  detecting movement of an in vivo oscillator using one or more in vivo sensors, the one or more in vivo sensors being a micro-electromechanical system (MEMS) capable of measuring acceleration, the MEMS having a first dual-axis accelerometer and a second dual-axis accelerometer, and the MEMS having a mass equal to or less than approximately 500 mm³;

receiving information from at least one of the one or more sensors; and deciding whether to switch an implanted cardiac therapy device from a lower tier of anti-arrhythmia therapy to a higher tier of anti-arrhythmia therapy based at least in part on the information;

wherein the deciding includes determining whether the received information indicates that a patient has exceeded a predetermined acceleration; and wherein the predetermined acceleration has a substantial component perpendicular to the acceleration of earth's gravity.

9. An implantable cardiac therapy device comprising:

a micro-electromechanical system (MEMS) capable of measuring acceleration, the MEMS having a first dual-axis accelerometer and a second dual-axis accelerometer, the two axes of the first dual-axis accelerometer defining a first plane and the two axes of the second dual-axis accelerometer defining a second plane, and the first plane differing from the second plane;

a shocking circuit; and control logic operative to control the shocking circuit to deliver a shock based at least in part on acceleration measured by the MEMS;

wherein the control logic causes the shocking circuit to delivery a shock based if a component of the acceleration exceeds a predetermined value.

10. The device of claim 9, wherein the acceleration includes at least one type of acceleration selected from the group consisting of static acceleration and dynamic acceleration.

11. The device of claim 9, wherein the shocking circuit has an electrical connection to a defibrillation electrode.

12. The device of claim 9, further comprising means for delivering anti-tachycardia pacing therapy.

13. The device of claim 12, further comprising control logic capable of causing the means for delivering anti-tachycardia pacing therapy to halt delivery of anti-tachycardia pacing therapy.

14. An implantable cardiac therapy device comprising:

a micro-electromechanical system (MEMS) capable of measuring acceleration, the MEMS having a first dual-axis accelerometer and a second dual-axis accelerometer, the two axes of the first dual-axis accelerometer defining a first plane and the two axes of the second dual-axis accelerometer defining a second plane, and the first plane differing from the second plane;

a shocking circuit; and control logic operative to control the shocking circuit to deliver a shock based at least in part on acceleration measured by the MEMS;

wherein the control logic determines a tilt angle based on one or more components of the acceleration.

15. An implantable cardiac therapy device comprising:

a micro-electromechanical system (MEMS) capable of measuring acceleration, the MEMS having a first dual-axis accelerometer and a second dual-axis accelerometer, the two axes of the first dual-axis accelerometer defining a first plane and the two axes of the second dual-axis accelerometer defining a second plane, and the first plane differing from the second plane;

a shocking circuit; and control logic operative to control the shocking circuit to deliver a shock based at least in part on acceleration measured by the MEMS;

wherein the control logic compares a tilt angle to a predetermined angle.

16. An implantable device comprising:

a micro-electromechanical system (MEMS) capable of measuring acceleration; and logic capable of determining postural sway based at least in part on acceleration measured by the MEMS;

wherein the MEMS includes a first dual-axis accelerometer and a second dual-axis accelerometer; and wherein the two axes of the first dual-axis accelerometer define a first plane and the two axes of the second dual-axis accelerometer define a second plane and wherein the first plane differs from the second plane.

17. The device of claim 16, wherein the logic determines tilt as a function of time based at least in part on acceleration measured by the MEMS.

18. The device of claim 16, wherein the logic determines whether tilt increases, decreases or remains substantially constant over a time interval.

19. The device of claim 18, wherein the logic determines a risk of falling based at least in part on the determination of whether tilt increases, decreases or remains substantially constant over the time interval.

20. The device of claim 18, wherein the logic assigns a high risk of falling if tilt increases over the time interval.

21. The device of claim 18, wherein the logic assigns a low risk of falling if tilt decreases over the time interval.

22. The device of claim 16, wherein the first dual-axis accelerometer is on a single monolithic integrated circuit.

23. The device of claim 16, wherein the MEMS comprises one or more polysilicon springs that provide a resistance against acceleration forces.

24. An implantable device comprising:

a micro-electromechanical system (MEMS) capable of measuring acceleration; and logic capable of determining postural sway based at least in part on acceleration measured by the MEMS;

wherein the MEMS includes a first dual-axis accelerometer and a second dual-axis accelerometer; and wherein the MEMS occupies a volume equal to or less than approximately 500 mm³.

25. An implantable device comprising:

a micro-electromechanical system (MEMS) capable of measuring acceleration; and logic capable of determining postural sway based at least in part on acceleration measured by the MEMS;

wherein the MEMS includes a first dual-axis accelerometer and a second dual-axis accelerometer; and wherein the MEMS has a mass equal to or less than approximately 5 grams.

* * * * *